US011640286B2

(12) United States Patent
Sankaran et al.

(10) Patent No.: US 11,640,286 B2
(45) Date of Patent: May 2, 2023

(54) PRODUCTION-READY ATTRIBUTES CREATION AND MANAGEMENT FOR SOFTWARE DEVELOPMENT

(71) Applicant: EQUIFAX INC., Atlanta, GA (US)

(72) Inventors: Yuvaraj Sankaran, Atlanta, GA (US); Felipe Ernesto Castillo Carvajal, Atlanta, GA (US); Carlos Augusto Pinzon Pinto, Alpharetta, GA (US); Gerardo Jorge Villarroel Gonzalez, Chile (CL); Pablo Andres Martinez Castro, Chile (CL)

(73) Assignee: EQUIFAX INC., Atlanta, GA (US)

( * ) Notice: Subject to any disclaimer, the term of this patent is extended or adjusted under 35 U.S.C. 154(b) by 19 days.

(21) Appl. No.: 17/418,740

(22) PCT Filed: Dec. 30, 2019

(86) PCT No.: PCT/US2019/068916
§ 371 (c)(1),
(2) Date: Jun. 25, 2021

(87) PCT Pub. No.: WO2020/142417
PCT Pub. Date: Jul. 9, 2020

(65) Prior Publication Data
US 2022/0066749 A1 Mar. 3, 2022

Related U.S. Application Data

(60) Provisional application No. 62/786,665, filed on Dec. 31, 2018, provisional application No. 62/886,644, filed on Aug. 14, 2019.

(51) Int. Cl.
G06F 9/44 (2018.01)
G06F 8/60 (2018.01)
(Continued)

(52) U.S. Cl.
CPC .............. *G06F 8/60* (2013.01); *G06F 8/24* (2013.01); *G06F 8/36* (2013.01); *G06F 8/70* (2013.01); *G06F 8/73* (2013.01)

(58) Field of Classification Search
CPC ..... G06F 8/70; G06F 8/73; G06F 8/24; G06F 8/36; G06F 8/60
See application file for complete search history.

(56) References Cited

U.S. PATENT DOCUMENTS

2003/0009250 A1\* 1/2003 Resnick .................... G06F 8/24
700/94
2005/0234698 A1 10/2005 Pinto et al.
(Continued)

FOREIGN PATENT DOCUMENTS

EP 3239835 A1 11/2017

OTHER PUBLICATIONS

JP 4759848, "Information Extraction Device From Printing Plate Making Data" (translation), Aug. 31, 2011, 11 pgs < JP_4759848. pdf>.\*
JP 60116489, "Image Processing Apparatus, Image Processing Apparatus Control Method, and Program" (translation) Oct. 16, 2016, 28 pgs <JP_6016489.pdf >.\*
(Continued)

Primary Examiner — Tuan A Vu
(74) Attorney, Agent, or Firm — Kilpatrick Townsend & Stockton LLP

(57) ABSTRACT

In some aspects, a computing system can determine a set of attributes based on analyzing input data using attribute templates written in a production-ready programming language. The computing system can generate attribute definitions for the set of attributes using the attribute templates and deploy the attribute definitions for the set of attributes to a production environment of a software program. The software program is written in a programming language compatible with the production-ready programming language. The computing system can monitor the performance of the (Continued)

Figure 1:
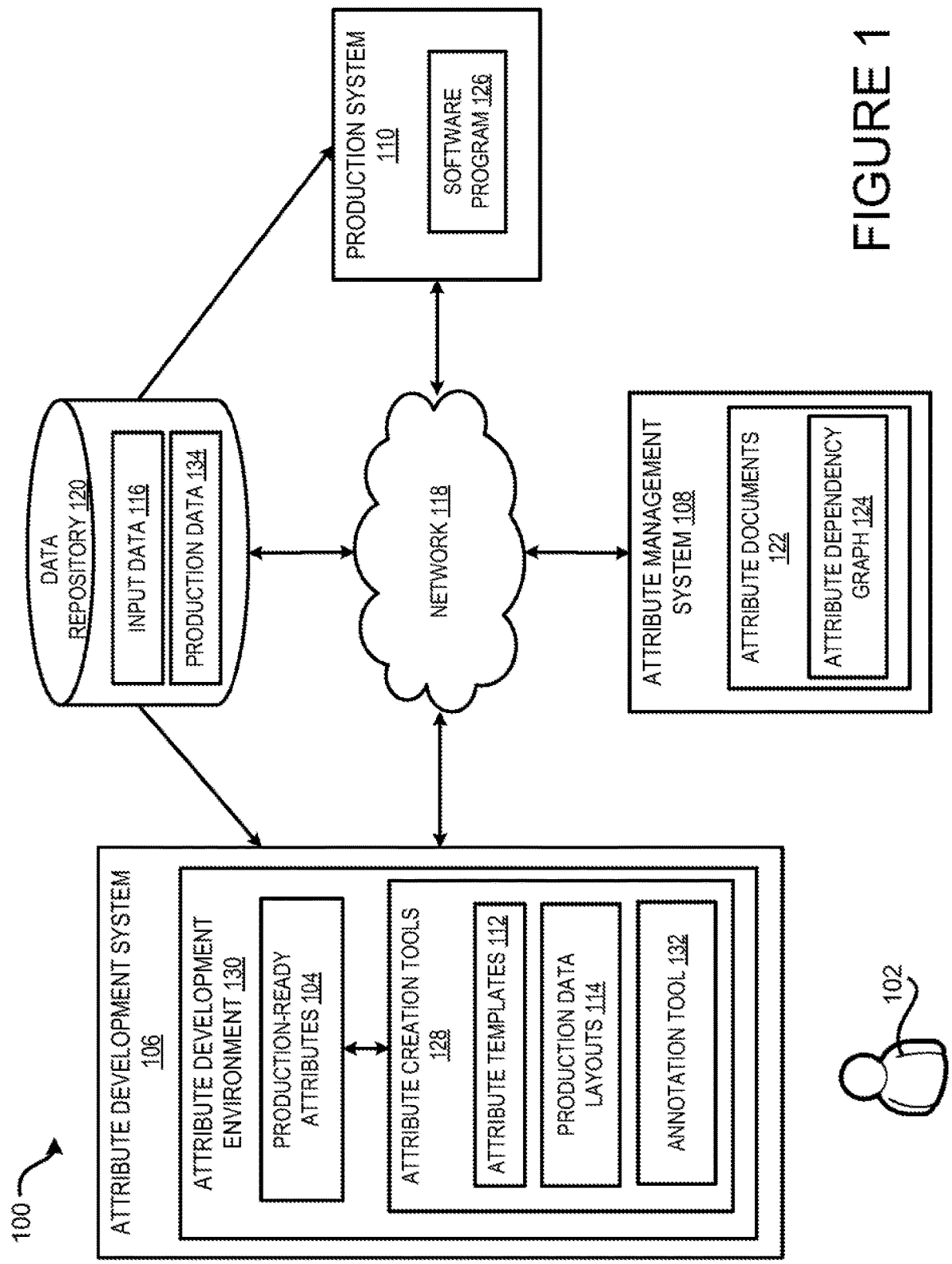

set of attributes in the production environment of the software program and cause the attribute definitions of the plurality of attributes to be modified based on the monitoring.

20 Claims, 6 Drawing Sheets

(51) Int. Cl.
  *G06F 8/36* (2018.01)
  *G06F 8/73* (2018.01)
  *G06F 8/70* (2018.01)
  *G06F 8/20* (2018.01)

(56) References Cited

U.S. PATENT DOCUMENTS

| | | |
|---|---|---|
| 2015/0019405 A1 | 1/2015 | Merrill et al. |
| 2017/0293472 A1* | 10/2017 | Catania .................. G06F 8/70 |
| 2018/0276342 A1 | 9/2018 | Curbera et al. |

OTHER PUBLICATIONS

International Application No. PCT/US2019/068916, "International Search Report and Written Opinion", dated May 12, 2020, 14 pages.
Sangeetha, et al., "Preprocessing Using Attribute Selection in Data Stream Mining", 3rd International Conference or Communication and Electronics Systems (ICCES), IEEE, Oct. 15, 2018, pp. 431-438.
IN202117033250, "First Examination Report", dated Jan. 9, 2023, 6 pages.

* cited by examiner

PRODUCTION-READY ATTRIBUTES CREATION AND MANAGEMENT FOR SOFTWARE DEVELOPMENT

CROSS REFERENCE TO RELATED APPLICATIONS

This claims priority to U.S. Provisional Application No. 62/786,665, entitled "Production-Ready Attributes Creation And Management For Software Development," filed on Dec. 31, 2018 and U.S. Provisional Application No. 62/886,644, entitled "Production-Ready Attributes Creation And Management For Software Development," filed on Aug. 14, 2019, each of which is hereby incorporated in its entirety by this reference.

TECHNICAL FIELD

This disclosure relates generally to software development, and more particularly relates to creating or managing software attributes without re-coding for software development and deployment.

BACKGROUND

New attributes used by software programs are often developed and deployed for production in a way that requires a set of steps where the logic of the attributes is re-implemented multiple times in different program environments. The logic of an attribute could include, for example, the operations or steps to be performed to generate a value for the attribute. For instance, attributes can be coded in an analytics-friendly language like SAS, documented in an electronic word processing or spreadsheet program, and re-implemented in a declarative and business-friendly tool that generates production-ready code. Although attribute logic should remain consistent from the original code creation to the production code generation, the various re-implementations of the code in different program environments are susceptible to human error, which can impact the functionality or efficiency of a software development process that generates code for a production environment.

SUMMARY

Various aspects of the present disclosure involve creating or managing software attributes without re-coding for software development and deployment. In one example, a computing system can include an attribute development system configured for accessing attribute templates and production data layouts. The attribute templates can be written in a production-ready programming language. The production data layouts can specify layouts for data used in a production environment of a software program. The software program can be written in a programming language that is compatible with the production-ready programming language. The attribute development system can also use the attribute templates to determine a set of attributes based on analyzing input data and generate attribute definitions for the set of attributes. The input data can be organized according to the production data layouts.

The computing system can further include a production system that is communicatively coupled to the attribute development system. In some examples, the production system is configured for implementing the production environment of the software program and deploying the attribute definitions for the set of attributes to the production environment of the software program. The computing system can also include an attribute management system that is communicatively coupled to the attribute development system and the production system. The attribute management system can monitor the performance of the set of attributes in the production environment of the software program. The attribute management system can also cause the attribute definitions of the set of attributes to be modified based on the monitoring.

This summary is not intended to identify key or essential features of the claimed subject matter, nor is it intended to be used in isolation to determine the scope of the claimed subject matter. The subject matter should be understood by reference to appropriate portions of the entire specification, any or all drawings, and each claim.

The foregoing, together with other features and examples, will become more apparent upon referring to the following specification, claims, and accompanying drawings.

BRIEF DESCRIPTION OF THE DRAWINGS

FIG. 1 depicts an example of an attribute creation and management system in which production-ready attributes can be created and managed to facilitate efficient development and deployment of a software program according to certain aspects of the present disclosure.

FIG. 2 depicts an example of a process for creating and managing production-ready attributes according to certain aspects of the present disclosure.

FIG. 3 depicts an example of a software development workflow without utilizing the creation and management of the production-ready attributes proposed herein.

FIG. 4 depicts an example of an improved software development workflow with production-ready attributes creation and management according to certain aspects of the present disclosure.

FIG. 5 depicts an example of a detection rule generator for generating synthetic identity detection rules based on a machine learning model according to certain aspects of the present disclosure.

FIG. 6 depicts an example of the relationship between the different systems in the improved software development model according to certain aspects of the present disclosure.

FIG. 7 depicts an example of a computing system suitable for implementing aspects of the techniques and technologies presented herein.

DETAILED DESCRIPTION

Certain aspects and features of the present disclosure involve creating and managing production-ready attributes for efficient software development and deployment. An attribute can include a component of a software program that can be utilized, along with other components of the software program, to implement the functionality for which the software is designed. For example, in a software program designed to implement a predictive model for risk assessment, an attribute can be a feature or a factor of the predictive model.

An attribute development system can provide an attribute development environment to a user, such as a statistician, so that the user can generate attributes in a production-ready language based on data layouts used in the production environment of the software program. The attribute development environment can provide attribute creation tools, such as software for developing attribute templates and production data layouts, to facilitate the user to create the production-ready attributes. For example, the attribute templates can be written, using a production-ready programming language, in a way that optimizes or otherwise improves the performance of the production-ready attributes in the production environment. A production-ready programming language can be a programming language that is compatible with the programming language used to develop and deploy the software program. Examples of the production-ready programming language can include, but are not limited to, Python programming language, Scala programming language, R programming language, and so on. In this way, the production-ready attributes can be deployed in the production environment without re-coding. Otherwise, the software code of the created attributes (written in a non-production-ready programming language) has to be written using the programming language used to develop and deploy the software program.

In addition, the attribute development environment can further provide tools to collect metadata of the production-ready attributes. These tools can allow an attribute management system to generate attribute documents, perform analysis based on the metadata, or both. For example, the attribute documents can include data describing the logic in the generated attributes, detecting duplicates in the attributes, building dependency graphs for the attributes, and so on. The dependency can include upstream dependencies, such as global definitions and data schemas, or downstream dependencies, such as scores, decision rules, products and delivery jobs, or the combination of both. Based on the attribute documents, regulation compliance or production environment compliance can be examined to provide approval for the production-ready attributes to be deployed in the production environment, if such approval is required. The attribute management system can further obtain performance data from the production environment and conduct performance analysis for the attributes. The results of the various analysis can be provided as feedback to the attribute development system to improve the generation of the production-ready attributes.

Certain aspects described herein address technical problems specific to software development and deployment. For instance, if existing attribute creation environments and systems are used to translate the originally created attributes to documents and to re-code those attributes using a production-ready language, these attribute creation environments and systems require users to master both the programming language used in the original attribute code and the production language to accomplish this task. Additionally or alternatively, the existing attributes creation environment and system can require a time-consuming validation process of the re-coded attributes. For example, the validation process may include multiple operations such as executing the original attributes and the re-coded attributes on input data and comparing the results. If there are mismatches in the results, the process further involves debugging, revising and re-testing. The validated attributes may then be deployed to the production system. The above process can take 6-9 months in some cases. This time-consuming validation process can hinder users' ability to develop and deploy the attributes to a production environment.

Aspects of the production-ready attributes creation and management presented herein address these technological problems by providing production-friendly attribute creation tools, such as attribute templates and production data layouts to allow users to create production-ready attributes with little efforts. These aspects can eliminate certain re-coding and translation steps in the software development process. Creating production-ready attributes from the beginning of the process significantly reduces the development and production time of a software program and also reduces the errors introduced in the process.

The above illustrative examples are given to introduce the reader to the general subject matter discussed here and are not intended to limit the scope of the disclosed concepts. The following sections describe various additional features and examples with reference to the drawings in which like numerals indicate like elements, and directional descriptions are used to describe the illustrative examples but, like the illustrative examples, should not be used to limit the present disclosure.

Operating Environment Example for Production-Ready Attributes Creation and Management System FIG. 1 is a block diagram depicting an example of an attribute creation and management system 100 in which production-ready attributes can be created and managed to facilitate efficient development and deployment of a software program, according to some aspects. The attribute creation and management system 100 is a specialized computing system that may be used for processing large amounts of data using a large number of computer processing cycles.

The attribute creation and management system 100 shown in FIG. 1 includes an attribute development system 106 that is configured for generating production-ready attributes 104, a production system 110 configured for integrating the production-ready attributes 104 into the production deployment of software program 126, and an attribute management system 108 configured for managing and monitoring the performance of the production-ready attributes 104. The attribute creation and management system 100 can further include a data repository 120 for storing input data 116 for the generation of the production-ready attributes 104 and production data 134 used by the software program 126 to generate production results.

The attribute development system 106 can present an attribute development environment 130 to a user 102, where the user 102 can analyze the input data 116 to determine attributes based on the input data 116 and to generate attribute definitions. The user 102 can be a data analyst, a statistician, or any individual who is tasked with performing analysis on the input data 116 to determine attributes for the software programs 126. The attribute development environment 130 can include user interfaces in which the user 102 can write, modify, compile, execute software codes to perform analysis on the input data 116 and to determine attributes and create attribute definitions based on the analysis.

An attribute or an attribute definition can include software code that can be utilized, along with other components of the software program, to realize the functionality for which the software is designed. In some cases, an attribute can also include the property or feature calculated or otherwise extracted from the input data 116 by executing the component of the software. A production-ready attribute 104 can be an attribute definition that can be integrated into the production deployment of the software program 126 without re-coding.

To facilitate the creation of production-ready attributes 104, the attribute development environment 130 supports the coding of the attributes in the production-ready programming language. In some aspects, the production-ready programming language can be a programming language that is compatible with the programming language used to develop and deploy the software program 126. Examples of the production-ready programming language can include, but are not limited to, Python programming language, Scala programing language, R programming language, and so on. The attribute development environment 130 can also provide attribute creation tools 128 to speed up the creation process of the production-ready attributes 104. For instance, the attribute creation tools 128 can include attribute templates 112 based on which the user 102 can create, with little effort, attribute definitions that are production ready. An attribute template 112 can include software codes that implement certain functionalities to compute an attribute. In an example where an attribute is determined to be the average value of a set of numbers, the attribute template can include the software code written in the production-ready language that includes steps and functions to calculate the average value of an input set of numbers. The user 102 can customize the attribute template 112 to include information that is specific to the input data 116 under analysis. For example, if the input data 116 contains a risk file of a consumer and the attribute is to be calculated based on the amount of loans that the consumer has, the user 102 can customize the above attribute template 112 based on the risk file so that the relevant values, such as the amount of various loans of the consumer, can be determined and used to calculate the attributes.

In some aspects, the attribute templates 112 are created in a way that optimizes or otherwise improved the runtime performance of the production-ready attributes 104. For instance, the attribute templates 112 can be coded in a way that improves the execution of the attribute definitions in the production deployment. As an example of this improved execution, the attribute template 112 can be written in a way that, compared with alternative implementations, has a smaller size, consumes less memory, executes more rapidly, performs fewer input/output operations, or some combination thereof.

In addition to the attribute templates 112, the attribute creation tools 128 can further include production data layouts 114 that are to be enforced in the attribute development environment 130. The production data layouts 114 specify the layouts for the input data 116 that are compatible with what is used or to be used in the production deployment. For example, the production data layouts 114 can specify that the input data of a credit file of a consumer are organized to include a set of ordered fields such as the name and age of the customer, bank accounts of the customer, credit cards of the customer, loans under the customer's name, and so on. The production data layouts 114 can be specified in scripted languages such as extensible markup language (XML), or in an open-standard file format such as javascript object notation (JSON) or AVRO that are supported in modern big data based analytical sandboxes as well as in production fulfillment environments.

Further attribute creation tools 128 can be provided in the attribute development environment 130 to facilitate the creation of production-ready attributes 104. For example, tools can be included to enforce entity level logic for the calculations of attributes, e.g., to enforce the data associated with an entity and used in the attribute development environment 130 to be identical to the data associated with the same entity when used in the production system 110. This helps to prevent coding approaches that will not be logically compatible with the production restrictions. Attributes created using these attribute creation tools 128 are production ready in that they can be easily integrated into the product deployment of the software program 126 without re-coding the attributes using the production language or without re-coding the attributes to accommodate the production data layouts 114.

In an example that involves risk analysis, the software program 126 can include a predictive model for predicting the risks of consumers defaulting on loans. Attributes, or features in this example, can be created so that the predictive model can use these attributes to perform the prediction. To determine the attributes, a user 102, such as a statistician or a data analyst, can use the attribute development system 106 to analyze input data 116 associated with consumers to determine attributes or features that are predictive to the risk of the consumers' default. The input data 116 can include risk data associated with the consumers, such as data obtained from credit records, credit files, financial records, or any other data that can be used for assessing the risk of a consumer defaulting on a loan.

The user 102 can perform various statistical analysis on the input data 116 for a consumer, such as determining the number of bank accounts a consumer has, the number of credit cards that the consumer has opened, the total amount of loans under the consumer's name, the number of bankruptcies, and so on. As discussed above, the analysis can be performed in the attribute development environment 130 using the attribute creation tools 128 that are written in the production language. For example, the user interface of the attribute development environment 130 can be used to write software code that invokes an attribute template 112 for calculating the number of bankruptcies of a consumer based on the input data 116 that are formatted according to the production data layouts 114. Similarly, the user interface can be used to write software code that invokes other attribute templates 112 to perform other analyses. Based on the analysis results, a user 102 or a software module built based on tools provided by the attribute development environment 130 can identify the attributes or features that are predictive of the risk associated with the consumers and send these attributes to the production system 110.

The production system 110 is configured for hosting a production environment in which the software program 126 is deployed and executed. In this production environment, attributes can be production ready if, for example, the programming language used in creating the attributes is compatible with the production environment of the production system 110, if the data format used in the attributes follows the production data layouts 114, or both. The production system 110 can, therefore, integrate these attributes into the software program 126 without re-coding. As a result, the production system 110 can seamlessly deploy the production-ready attributes 104 to the software program 126 for use in the production. In the above example, the deployment allows the predictive model to use the newly created production-ready attributes 104 to perform risk prediction based on the production data 134 associated with a consumer under analysis. In other examples, there are additional requirements for attributes to be production-ready. The additional requirements include, for example, software performance be compatible with the production environment, security reviews of the code to ensure no vulnerabilities are introduced in the production environment, and legal and compliance reviews to ensure that attributes used do not violate any regulatory, contractual or policy restrictions. The technologies presented herein can be utilized to integrate with other systems to ensure the additional requirements are met to generate production-ready attributes.

Using the attribute creation tools 128 in the attribute development environment 130 with the production data layouts 114 can achieve data schema alignment. For instance, data structures used in the development process are aligned with the data structures used for production fulfillment. In addition, environment configuration alignment can be achieved by using attribute templates 112 built to account for the environment configuration alignment. For instance, environment level dependencies outside of the deployed attributes can be aligned with the development environment.

As shown in FIG. 1, the attribute creation and management system 100 further includes the attribute management system 108 for managing the creation and use of the production-ready attributes 104. In one implementation, the attribute management system 108 can generate one or more attribute documents 122 that describe various aspects of the production-ready attributes 104. For example, the attribute documents 122 can describe the production-ready attributes 104, global variables or values used in the production-ready attributes 104, attribute templates 112 used to create the production-ready attributes 104, aggregations of the production-ready attributes 104, the dependencies among the production-ready attributes 104 and so on.

In order to generate the attribute documents 122, the attribute management system 108 can analyze the metadata in the production-ready attributes 104. The metadata of the production-ready attributes 104 describes various types of information. Examples of information described by the metadata include the input data 116 used to generate the production-ready attributes 104, the global variables or macros used in each of the production-ready attributes 104, the attribute templates 112 used to generate the production-ready attributes 104, other production-ready attributes 104 on which the current production-ready attribute 104, the standard functions or library called in the production-ready attributes 104, the version of the library, etc. The metadata can be collected at the attribute development system 106 by including an annotation tool 132 in the attribute creation tools 128 to enforce annotations in the production-ready attributes 104 when creating the production-ready attributes 104.

For example, the annotation tool 132 can provide an annotation framework in each of the production-ready attributes 104 and the framework can contain pre-defined fields formatted in a certain way for the user 102 to input metadata. Examples of these pre-defined fields, include a field at the beginning of the production-ready attribute 104 to record the author of the production-ready attribute 104, a field after each section of the code that describes the operations performed in that section and other production-ready attributes 104 invoked in that section, etc.

Alternatively, or additionally, the annotation tool 132 can automatically detect and fill in certain fields of metadata. For instance, the annotation tool 132 can detect the version of the production-ready attributes 104 based on the historical records of the production-ready attribute 104 in the attribute development environment 130. The annotation tool 132 can also scan and search the production-ready attribute 104 for keywords that represent global variables, macros, functions or public libraries, and annotate the corresponding portion with the identified keywords. The annotation tool 132 can also determine the attribute template 112 used to create the production-ready attribute 104 and annotate the production-ready attributes 104 with this information accordingly.

The annotation of metadata can be performed as the production-ready attributes 104 are being created or after the production-ready attributes 104 have been created. The metadata can be presented in the user interface of the attribute development environment 130 using a certain type of font, in a different color than the rest of the code, following by a certain type of symbols (e.g., a double slash), or some combination thereof.

Based on the annotation of the metadata in the production-ready attributes 104, the attribute management system 108 can extract some of the metadata, such as by detecting the symbols used to indicate an annotation, and generate the attribute documents 122. For other metadata, such as the dependencies among the production-ready attributes 104, the attribute management system 108 can determine such metadata based on the attribute documents 122 or the source code of the production-ready attributes, and build an attribute dependency graph 124. The attribute dependency graph 124 is a data structure that allows the attribute management system 108 to determine the relationship among the production-ready attributes 104 and to determine the impact of a change in a production-ready attribute 104 on other production-ready attributes 104. Such information can be provided as a feedback to the attribute development system 106, for example, presented in a user interface, to facilitate the user 102 in determining new attributes to avoid interfering the existing production-ready attributes 104, to reuse certain production-ready attribute 104 without creating a new one, or both.

In addition to the dependencies among production-ready attributes 104, the attribute documents 122 can further facilitate the identification of direct and indirect dependencies among other elements, such as fields, segments, global variables or values used in the production-ready attributes 104, etc. The attribute documents 122 can be utilized to perform various analyses such as attributes comparison to determine how similar or different are the dependencies used to compute the attributes being compared. In some aspects, the attribute comparison can also be performed using data, instead of or in addition to the metadata in the attribute documents 122. For example, the attribute comparison can be performed based on the calculation of the attribute logic against a representative data sample. In further implementations, visual side-by-side exploration of the code of the attributes can be performed to identify similarities and differences of the attribute implementations. In this way, the differences and similarities of a set of attributes can be identified, qualified and quantified.

In addition, the attribute management system 108 can detect, based on the attribute documents 122 and the production-ready attributes 104, duplicates in the production-ready attributes 104. For example, the attribute management system 108 can analyze the source code of the production-ready attributes 104 to determine that one production-ready attribute 104 is very similar to another production-ready attribute 104 in terms of their source codes. The attribute management system 108 can also determine that the global variables or values or production-ready attributes 104 that a production-ready attribute 104 depends on substantially overlap with that of another production-ready attributes 104. The attribute management system 108 can further analyze the input data 116 used by the production-ready attributes 104 to determine a duplicate. If the input data 116 used by two production-ready attributes 104 are the same or very similar, then it is likely that these two production-ready attributes 104 are duplicates. Another way of identifying duplicates is to compare the results of the computation of these attributes against the same baseline input data set. For example, if two attributes return the same output value when given the same input values for a large-representative data set, they are more likely to be duplicates from each other.

Various other factors can be considered to detect the attributes duplicates. Duplicates in global variables or values can be detected similarly.

Based on one or more of these factors, the attribute management system 108 can generate a list of potential duplicates among global variables or values and production-ready attributes 104. The list of potential duplicates can be, for example, presented to the user 102 to verify the duplication. Alternatively, or additionally, the attribute management system 108 can provide suggestion for code optimization to the user 102 or the software developers of the software program 126, such as to eliminate the code involving a duplicate production-ready attribute 104, to simplify the predictive model of the software program to remove the duplicate production-ready attribute 104, and so on.

The list of potential duplicates and other attribute documents 122 can further be provided to the attributes management team for approval regarding the potential duplicates, project size, and so on. In applications where the use of the software program 126 and the data is highly regulated, the attribute management system 108 can also perform a review or initial screening for regulation, contractual and policy compliance. In some aspects, these approval procedures are required prior to deploying the production-ready attributes 104 to the production system 110, while in other implementations, these approval procedures are optional.

The attribute management system 108 can monitor the use and performance of the production-ready attributes 104, as deployed in the production system 110 for use in the software program 126, to generate a performance profile. For example, the attribute management system 108 can measure different runtime performance indicators of the production-ready attributes 104 and the software program 126. The attribute management system 108 can measure these runtime performance indicators to determine if the runtime performance, such as the time it takes for the system to complete the calculations required by these attributes, is compatible with the production environment.

The attribute management system 108 can also analyze the performance of the production-ready attributes 104 in terms of the predictability of these production-ready attributes 104. For example, the attribute management system 108 can track the consistency of the statistical distributions of these attributes over time. These statistical distributions could show significant variations in the behavior of these attributes that could have an impact on their predictability. For example, if a change in the value of an attribute defined by the production-ready attribute 104 has little impact on the prediction outcome, this attribute is not predictive as expected and feedback can be generated for the user 102 to re-consider including the attributes in the predictive model. The performance data can be obtained by the attribute management system 108 actively requesting performance data from the production system 110, by configuring the production system 110 to periodically send performance data to the attribute management system 108, or by some combination of these operations.

As shown in FIG. 1, the various systems of the attribute creation and management system 100 can communicate with each other through a network 118, such as a public data network, a private data network, or some combination thereof. A data network may include one or more of a variety of different types of networks, including a wireless network, a wired network, or a combination of a wired and wireless network. Examples of suitable networks include the Internet, a personal area network, a local area network ("LAN"), a wide area network ("WAN"), or a wireless local area network ("WLAN"). A wireless network may include a wireless interface or a combination of wireless interfaces. A wired network may include a wired interface. The wired or wireless networks may be implemented using routers, access points, bridges, gateways, or the like, to connect devices in the data network.

A data network may include network computers, sensors, databases, or other devices that may transmit or otherwise provide data to attribute creation and management system 100. For example, a data network may include local area network devices, such as routers, hubs, switches, or other computer networking devices. The data networks depicted in FIG. 1 can be incorporated entirely within (or can include) an intranet, an extranet, or a combination thereof. In one example, communications between two or more systems or devices can be achieved by a secure communications protocol, such as secure Hypertext Transfer Protocol ("HTTPS") communications that use secure sockets layer ("SSL") or transport layer security ("TLS"). In addition, data or transactional details communicated among the various computing devices may be encrypted. For example, data may be encrypted in transit and at rest.

The number of systems and devices depicted in FIG. 1 is provided for illustrative purposes. Different numbers of devices may be used. For example, while certain devices or systems are shown as single devices in FIG. 1, multiple devices may instead be used to implement these devices or systems. Likewise, while the attribute development system 106, the attribute management system 108, and the production system 110 are shown to be implemented on separate devices, two or more of these systems can be implemented on the same device.

The attribute creation and management system 100 may also include one or more network-attached storage units on which various repositories, databases, or other data structures are stored. Examples of these data structures are the data repository 120. Network-attached storage units may store a variety of different types of data organized in a variety of different ways and from a variety of different sources. For example, the network-attached storage unit may include storage other than the primary storage located within the attribute development system 106 that is directly accessible by processors located therein. In some aspects, the network-attached storage unit may include secondary, tertiary, or auxiliary storage, such as large hard drives, servers, virtual memory, among other types. Storage devices may include portable or non-portable storage devices, optical storage devices, and various other mediums capable of storing and containing data. A machine-readable storage medium or computer-readable storage medium may include a non-transitory medium in which data can be stored and that does not include carrier waves or transitory electronic signals. Examples of a non-transitory medium may include, for example, a magnetic disk or tape, optical storage media such as a compact disk or digital versatile disk, flash memory, memory or memory devices.

Examples of Attribute Creation and Management Operations

Figure 2:
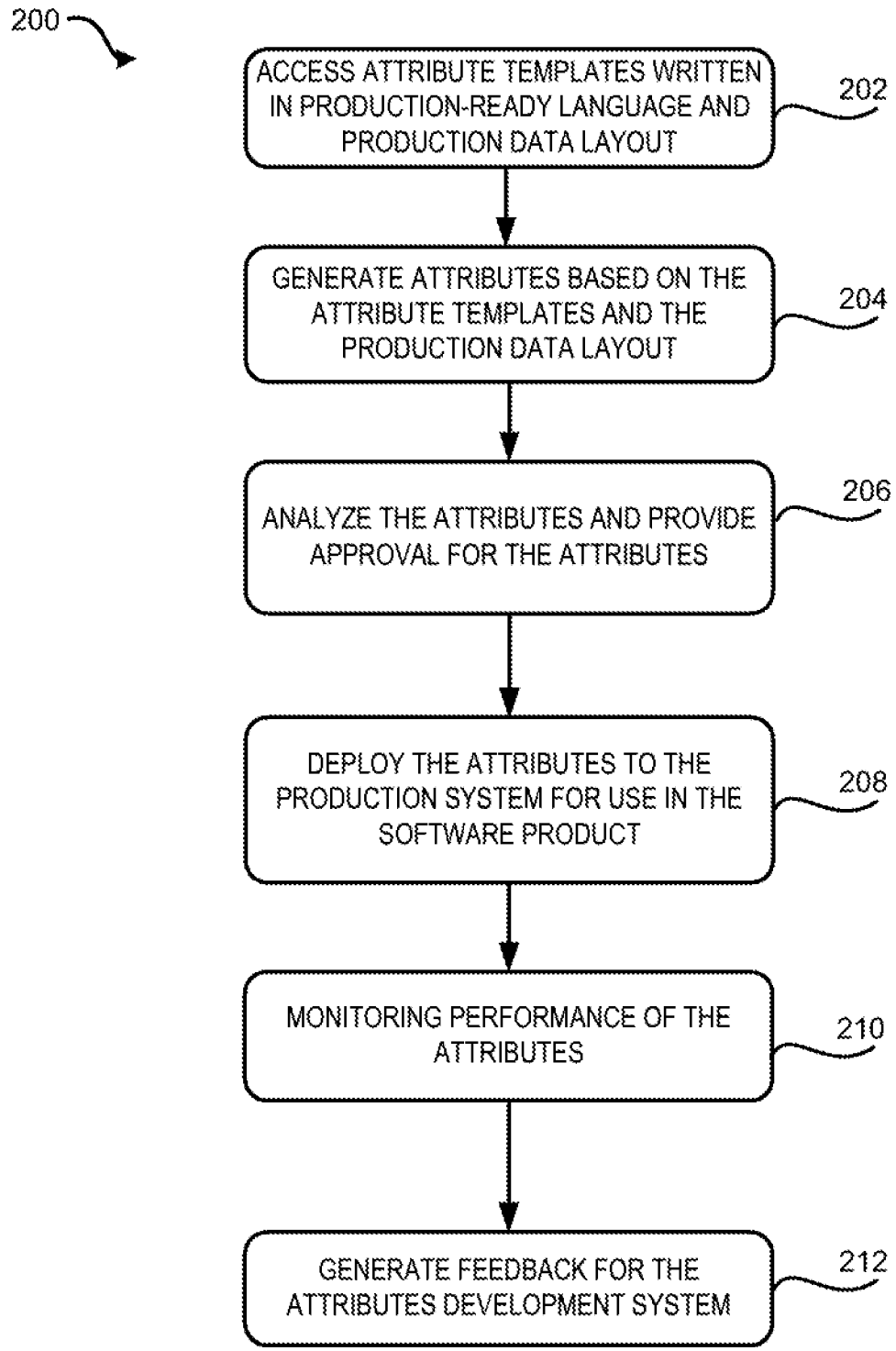

The attribute creation and management system 100 can execute one or more processes to perform production-ready attributes creation and management. FIG. 2 is a flowchart illustrating an example of a process 200 for creating and managing production-ready attributes. For illustrative purposes, the process 200 is described with reference to implementations described above with respect to one or more examples described herein. Other implementations, however, are possible. In some aspects, the steps in FIG. 2 may be implemented in program code that is executed by one or more computing devices such as the attribute development system 106 and the attribute management system 108 depicted in FIG. 1. In some aspects of the present disclosure, one or more operations shown in FIG. 2 may be omitted or performed in a different order. Similarly, additional operations not shown in FIG. 2 may be performed.

At block 202, the attribute development system 106 accesses and presents attribute creation tools 128 to a user 102 such as the attribute templates 112 and the production data layouts 114. In one example, the attribute template 112 can be written in a production-ready language so that the attribute definitions built based on the attribute templates 112 are also in the production-ready language. The production data layouts 114 specify the data layouts used by the production system 110 when executing the software program 126.

At block 204, the attribute development system 106 generates production-ready attributes 104 based on the attribute templates 112 and the production data layouts 114 as well as the user inputs. As discussed above, the user interface provided by the attribute development environment 130 can be utilized by the user to write software code based on the attribute templates 112 to perform various tasks such as analyzing the input data 116. Based on the analysis, the user 102 can determine production-ready attributes 104 that are to be integrated into the software program 126. Alternatively, or additionally, the attribute development environment 130 can automatically select the production-ready attributes 104 based on one or more criteria specified by the user 102.

At block 206, the process 200 involves analyzing the production-ready attributes 104 and providing approval for the production-ready attributes 104. The attribute management system 108 can perform the analysis by generating attribute documents 122 based on the metadata contained in the production-ready attributes 104 and examining the attribute documents 122. The metadata can be provided by the user 102 or extracted from the code or both when building the production-ready attributes 104, automatically generated and inserted into the production-ready attributes 104 by the attribute development environment 130, or both. The metadata, and thus the attribute documents 122, can include, but are not limited to, the input data 116 used to generate the production-ready attributes 104, the global variables or macros used in each of the production-ready attributes 104, the attribute templates 112 used to generate the production-ready attributes 104, other production-ready attributes 104 that the current production-ready attribute 104 depends on, the standard functions or library called in the production-ready attributes 104, the version of the library, and so on. Based on the attribute documents 122, the attribute management system 108 can determine or facilitate to determine if the production-ready attributes 104 are approved for deployment with regard to the production environment compliance or regulatory compliance.

At block 208, the process 200 involves deploying the production-ready attributes 104 to the production system 110 so that the production-ready attributes 104 can be integrated into and used by the software program 126. For example, the attribute development system 106 can transmit the production-ready attributes 104 to the production system 110 for deployment. The production system 110 can modify the software program 126, such as a software program implementing a predictive model for risk prediction associated with granting a loan to a user, to incorporate the received production-ready attributes 104 so that the production-ready attributes 104 can be part of the factors for the prediction. Because the production-ready attributes 104 are created using a production-ready language and based on the production data layouts 114, they can be directly added to the software program 126 without re-coding.

At block 210, the process 200 involves monitoring the performance of the production-ready attributes 104. The attribute management system 108 can obtain performance data from the production system 110 by, for example, proactively requesting performance data or by configuring the production system 110 to send the performance data periodically or upon detecting a certain event. Based on the performance data, the attribute management system 108 can measure different runtime performance indicators of the production-ready attributes 104 and the software program 126 to determine if the runtime performance, such as the speed of generating results, is compatible with the production environment. The attribute management system 108 may further measure the predictability of the production-ready attributes 104.

At block 212, the process 200 involves generating feedback and providing the feedback to the attribute development system 106. For example, the attribute management system 108 can provide feedback on the performance of the production-ready attributes 104 to the attribute development system 106 so that the user 102 can determine whether and how to modify the production-ready attributes 104 to improve the performance. In addition, the attribute management system 108 can further provide feedback regarding the production-ready attributes 104 based on the analysis of the attribute documents 122. For instance, the attribute management system 108 can detect duplicates in the attributes, construct dependency graphs for the attributes, and so on as described above with respect to FIG. 3. These analysis results can facilitate the user 102 to make decisions such as removing duplicate attributes from the current prediction model, re-using existing attributes, combining two attributes, removing non-predictive attributes, and so on.

Figure 3:
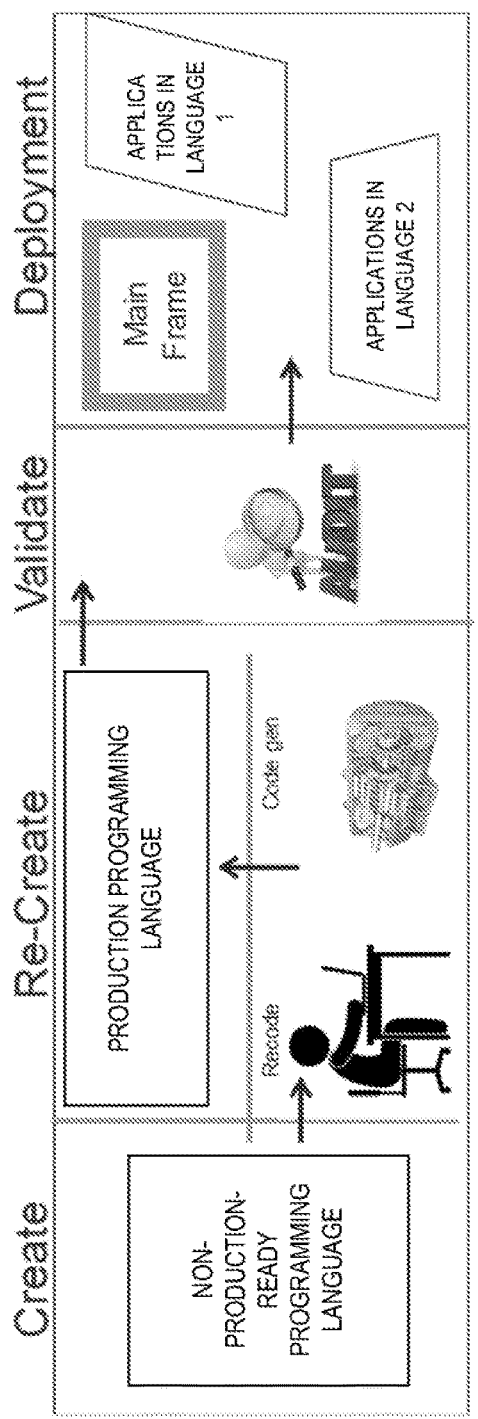

FIG. 3 depicts an example of a software development workflow without utilizing the creation and management of the production-ready attributes proposed herein. As shown in FIG. 3, the process involves creating attributes using a non-production-ready language, such as SAS, that is incompatible with the production programming language used in the deployment stage, such as C++ or Java language. As a result, the attributes have to be translated into documents containing the definition of the attributes which are then recreated or re-coded in a production programming language, such as the C++ language, Java language or assembly language so that they can be deployed in applications written in these production languages. Because these multiple steps of translation are prone to human error, validation needs to be performed to verify that the re-coded attributes are the same as the originally created attributes. The validation process can involve executing the original attributes and the re-coded attributes on the input data 116 and comparing the results. If there are mismatches in the results, the process further involves debugging, revising and re-testing. The validated attributes may then be deployed to the production system 110. The above process can take 6-9 months in some cases.

Figure 4:
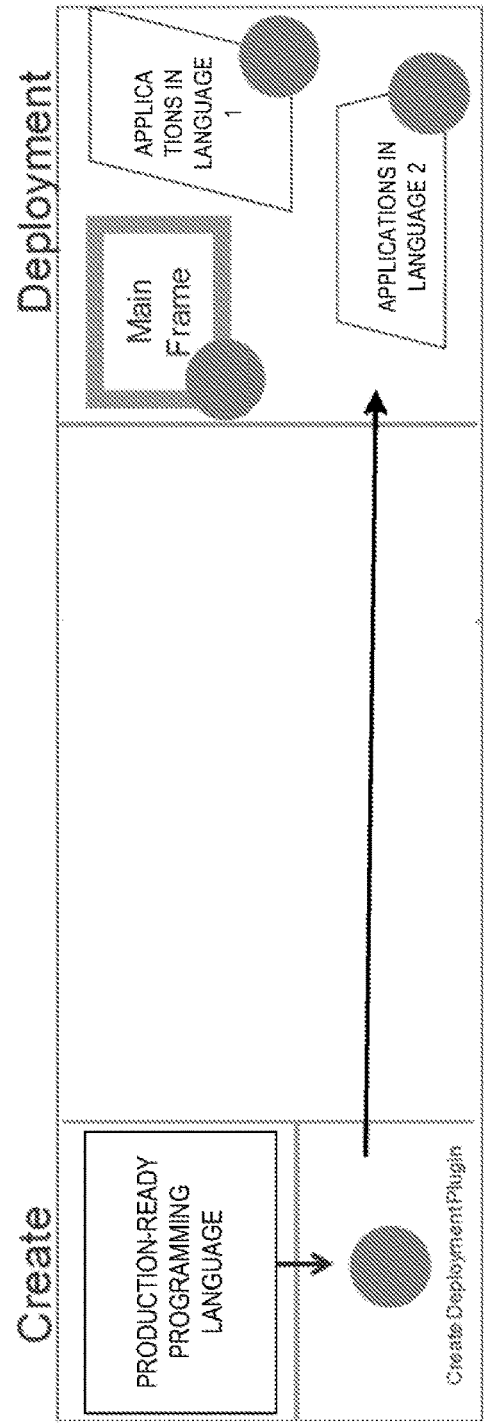

FIG. 4 depicts an example of an improved software development workflow with the production-ready attributes creation and management according to the disclosure presented herein. The production Compared with the workflow shown in FIG. 3, the improved workflow eliminates the time-consuming re-creation stage and the validation stage.

Because the production-ready attributes 104 are created from the beginning, they can be seamlessly integrated into the production environment without re-coding. As a result, the time of the entire process can be significantly reduced, e.g., less than one month.

Figure 5:
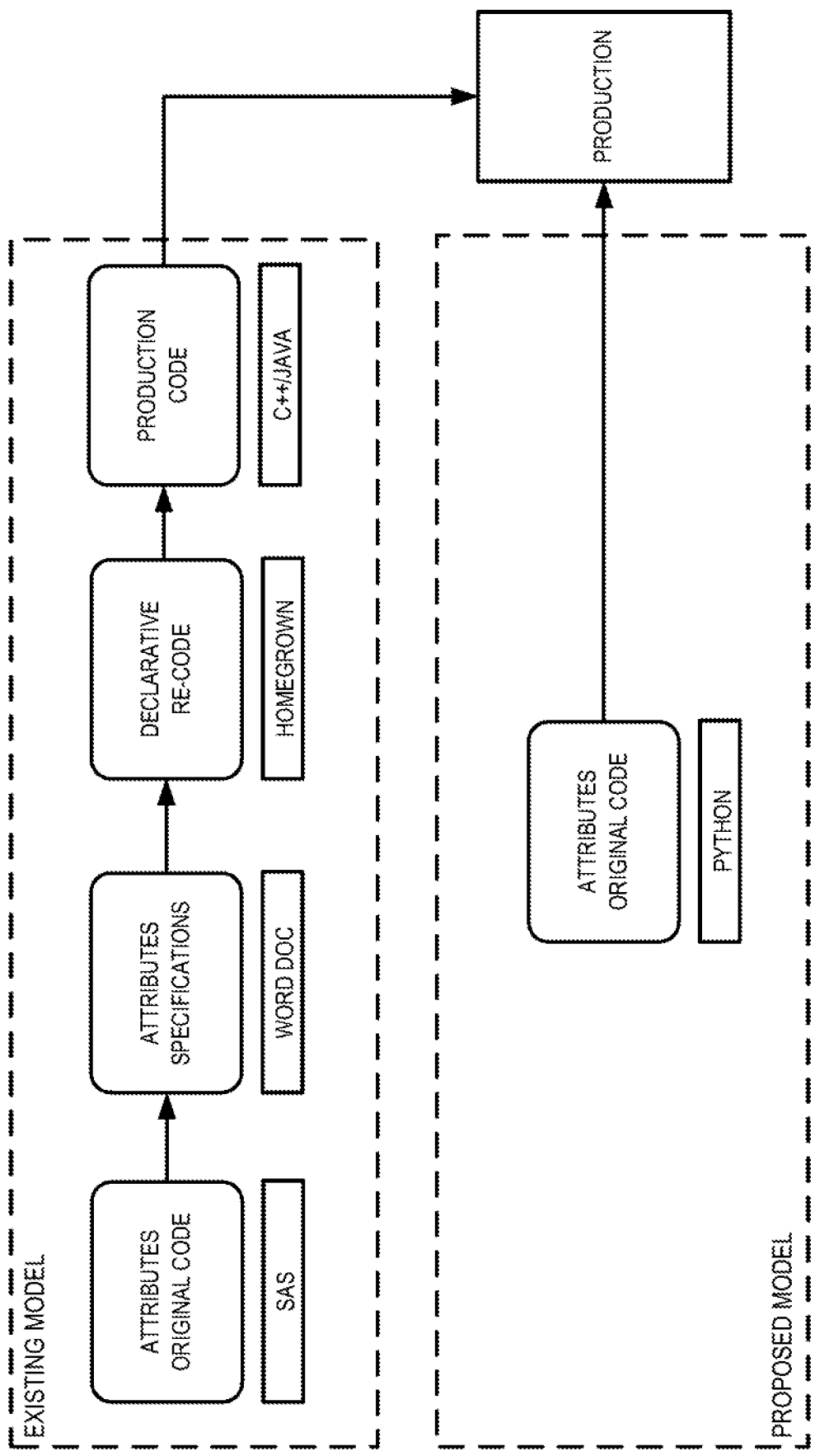

FIG. 5 depicts an example of a comparison between the documents generated in an existing software development model and an improved model with the proposed production-ready attributes creation and management. As shown in FIG. 5, under the existing model, multiple documents need to be produced, including the attributes' original code, to capture the calculation logic in the attributes (e.g., a SAS file), attributes specification documents to capture the consumer or business level logic (e.g., in a word file), declarative re-code to conform to the production data layout, and production code to implement the attributes in the production language (e.g., a C++ or Java file). Compared with these documents, the improved model only contains the production-ready attributes 104 written in a production-ready language, such as Python, and they can be readily deployed to the production environment.

Figure 6:
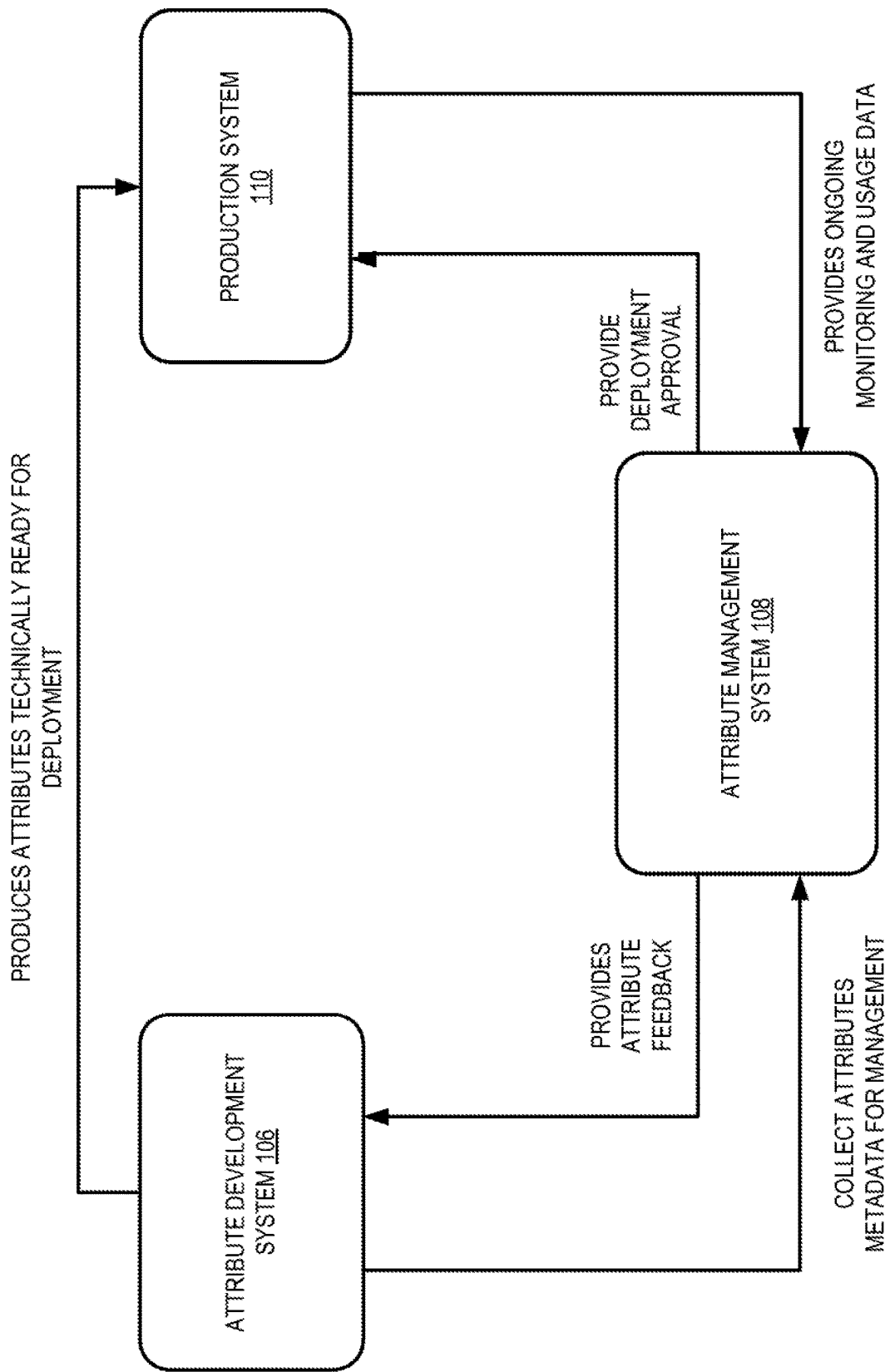

FIG. 6 depicts an example of a relationship between the different systems in an improved software development model depicted in FIG. 5. As shown in FIG. 6, the attribute development system 106 provides an attributes development framework with guardrails and utilities, such as the attribute creation tools 128, that allow users 102 to code attributes that are ready for production deployment. The attribute development system 106 can provide the production-ready attributes 104 to the production system 110. The production system 110 provides artifacts and services that allow the integration of the newly created production-ready attributes 104 into the production fulfillment flow.

The attribute development system 106 also collects and provides attributes metadata to the attribute management system 108. Based on the collected attribute metadata, the attribute management system 108 generates attribute documents 122 and provides a tool that allows users 102 to access the documents and other management features without the need to re-implement the metadata of the production-ready attributes 104. Based on the attribute metadata, the attribute management system 108 also performs analysis and provides deployment approval to the production system 110. The attribute management system 108 further receives monitoring and usage data from the production system 110 and provides attributes feedback to the attribute development system 106 based on the attribute documents 122 and the monitoring and usage data.

Figure 7:
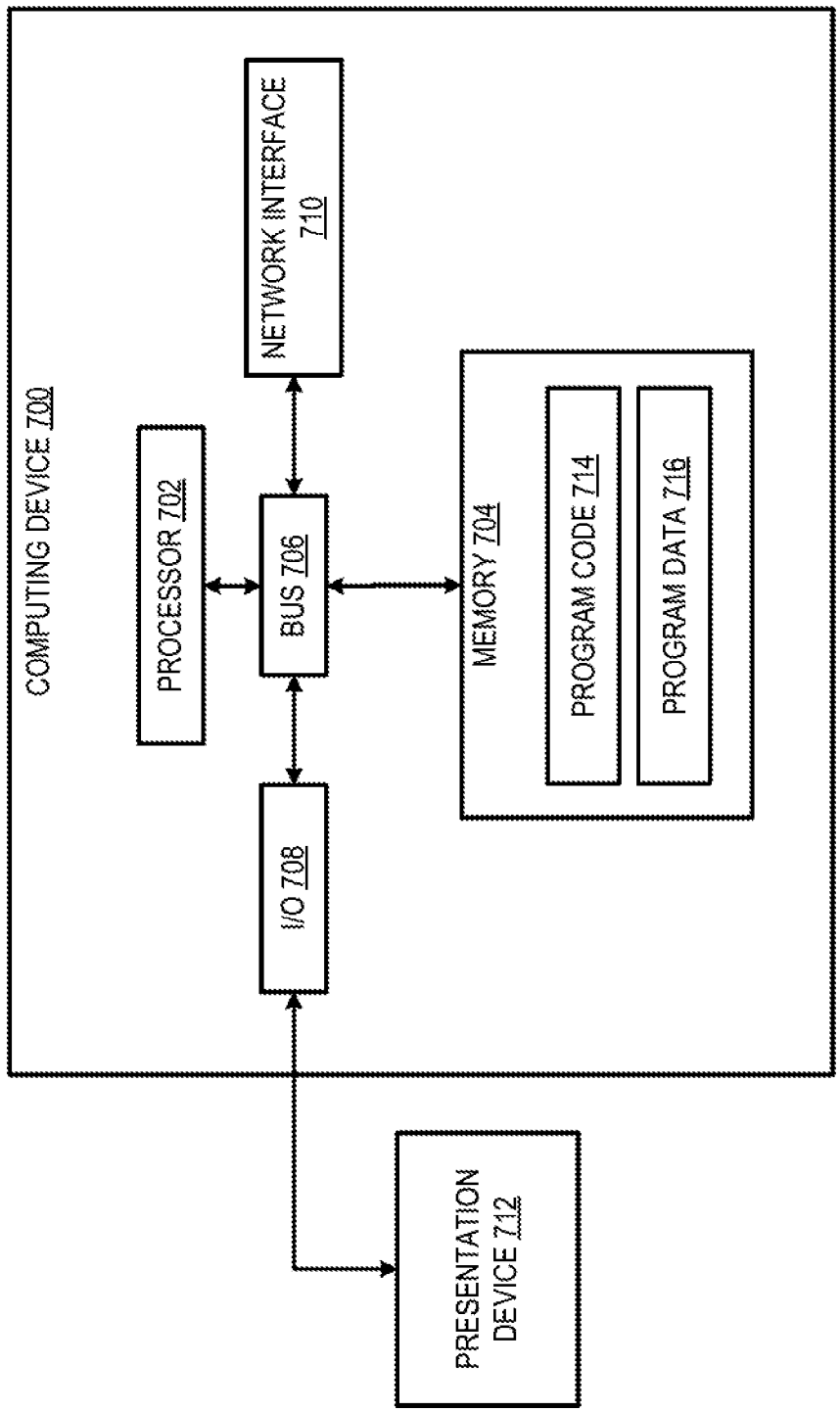

Example of Computing Environment for Production-Ready Attributes Creation and Management Any suitable computing system or group of computing systems can be used to perform the operations for the production-ready attributes creation and management described herein. For example, FIG. 7 is a block diagram depicting an example of a computing device 700, which can be used to implement the attribute development system 106, the attribute management system 108 or the production system 110. The computing device 700 can include various devices for communicating with other devices in the attribute creation and management system 100, as described with respect to FIG. 1. The computing device 700 can include various devices for performing one or more attributes creation and management operations described above with respect to FIGS. 1-6.

The computing device 700 can include a processor 702 that is communicatively coupled to a memory 704. The processor 702 executes computer-executable program code stored in the memory 704, accesses information stored in the memory 704, or both. Program code may include machine-executable instructions that may represent a procedure, a function, a subprogram, a program, a routine, a subroutine, a module, a software package, a class, or any combination of instructions, data structures, or program statements. A code segment may be coupled to another code segment or a hardware circuit by passing or receiving information, data, arguments, parameters, or memory contents. Information, arguments, parameters, data, etc. may be passed, forwarded, or transmitted via any suitable means including memory sharing, message passing, token passing, network transmission, among others.

Examples of a processor 702 include a microprocessor, an application-specific integrated circuit, a field-programmable gate array, or any other suitable processing device. The processor 702 can include any number of processing devices, including one. The processor 702 can include or communicate with a memory 704. The memory 704 stores program code that, when executed by the processor 702, causes the processor to perform the operations described in this disclosure.

The memory 704 can include any suitable non-transitory computer-readable medium. The computer-readable medium can include any electronic, optical, magnetic, or other storage device capable of providing a processor with computer-readable program code or other program code. Non-limiting examples of a computer-readable medium include a magnetic disk, memory chip, optical storage, flash memory, storage class memory, ROM, RAM, an ASIC, magnetic storage, or any other medium from which a computer processor can read and execute program code. The program code may include processor-specific program code generated by a compiler or an interpreter from code written in any suitable computer-programming language. Examples of suitable programming language include Hadoop, C, C++, C#, Visual Basic, Java, Python, Perl, JavaScript, ActionScript, etc.

The computing device 700 may also include a number of external or internal devices such as input or output devices. For example, the computing device 700 is shown with an input/output interface 708 that can receive input from input devices or provide output to output devices. A bus 706 can also be included in the computing device 700. The bus 706 can communicatively couple one or more components of the computing device 700.

The computing device 700 can execute program code 714 such as the attribute development environment 130, the program code implementing attributes management on the attribute management system 108, or the software program 126. The program code 714 may be resident in any suitable computer-readable medium and may be executed on any suitable processing device. For example, as depicted in FIG. 7, the program code 714 can reside in the memory 704 at the computing device 700 along with the program data 716 associated with the program code 714, such as the attribute templates 112, production data layouts 114, or the attribute documents 122. Executing the program code 714 can configure the processor 702 to perform the operations described herein.

In some aspects, the computing device 700 can include one or more output devices. One example of an output device is the network interface device 710 depicted in FIG. 7. A network interface device 710 can include any device or group of devices suitable for establishing a wired or wireless data connection to one or more data networks described herein. Non-limiting examples of the network interface device 710 include an Ethernet network adapter, a modem, etc.

Another example of an output device is the presentation device 712 depicted in FIG. 7. A presentation device 712 can include any device or group of devices suitable for providing visual, auditory, or other suitable sensory output. Non-limiting examples of the presentation device 712 include a touchscreen, a monitor, a speaker, a separate mobile computing device, etc. In some aspects, the presentation device 712 can include a remote client-computing device that communicates with the computing device 700 using one or more data networks described herein. In other aspects, the presentation device 712 can be omitted.

General Considerations

Numerous specific details are set forth herein to provide a thorough understanding of the claimed subject matter. However, those skilled in the art will understand that the claimed subject matter may be practiced without these specific details. In other instances, methods, apparatuses, or systems that would be known by one of ordinary skill have not been described in detail so as not to obscure claimed subject matter.

Unless specifically stated otherwise, it is appreciated that throughout this specification that terms such as "processing," "computing," "determining," and "identifying" or the like refer to actions or processes of a computing device, such as one or more computers or a similar electronic computing device or devices, that manipulate or transform data represented as physical electronic or magnetic quantities within memories, registers, or other information storage devices, transmission devices, or display devices of the computing platform.

The system or systems discussed herein are not limited to any particular hardware architecture or configuration. A computing device can include any suitable arrangement of components that provides a result conditioned on one or more inputs. Suitable computing devices include multipurpose microprocessor-based computing systems accessing stored software that programs or configures the computing system from a general purpose computing apparatus to a specialized computing apparatus implementing one or more aspects of the present subject matter. Any suitable programming, scripting, or other type of language or combinations of languages may be used to implement the teachings contained herein in software to be used in programming or configuring a computing device.

Aspects of the methods disclosed herein may be performed in the operation of such computing devices. The order of the blocks presented in the examples above can be varied—for example, blocks can be re-ordered, combined, or broken into sub-blocks. Certain blocks or processes can be performed in parallel.

The use of "adapted to" or "configured to" herein is meant as an open and inclusive language that does not foreclose devices adapted to or configured to perform additional tasks or steps. Additionally, the use of "based on" is meant to be open and inclusive, in that a process, step, calculation, or other action "based on" one or more recited conditions or values may, in practice, be based on additional conditions or values beyond those recited. Headings, lists, and numbering included herein are for ease of explanation only and are not meant to be limiting.

While the present subject matter has been described in detail with respect to specific aspects thereof, it will be appreciated that those skilled in the art, upon attaining an understanding of the foregoing, may readily produce alterations to, variations of, and equivalents to such aspects. Any aspects or examples may be combined with any other aspects or examples. Accordingly, it should be understood that the present disclosure has been presented for purposes of example rather than limitation, and does not preclude inclusion of such modifications, variations, or additions to the present subject matter as would be readily apparent to one of ordinary skill in the art.

The invention claimed is:

1. A system comprising:
an attribute development system configured for:
accessing attribute templates and production data layouts, wherein the attribute templates are written in a production-ready programming language, and wherein the production data layouts specify layouts for data used in a production environment of a software program,
determining a plurality of attributes based on analyzing input data using the attribute templates, the input data being organized according to the production data layouts, and
generating attribute definitions for the plurality of attributes using the attribute templates;
a production system communicatively coupled to the attribute development system, the production system configured for:
implementing the production environment of the software program, the software program written in a programming language compatible with the production-ready programming language, and
deploying the attribute definitions for the plurality of attributes to the production environment of the software program; and
an attribute management system communicatively coupled to the attribute development system and the production system, the attribute management system configured for:
monitoring performance of the plurality of attributes in the production environment of the software program, and
causing the attribute definitions of the plurality of attributes to be modified based on the monitoring.

2. The system of claim 1, wherein the attribute definitions are associated with metadata of the plurality of attributes, and wherein the attribute management system is further configured for:
analyzing the attribute definitions based on the metadata to generate an attribute dependency graph; and
causing the attribute definitions to be modified based on the attribute dependency graph.

3. The system of claim 1, wherein the attribute definitions are associated with metadata of the plurality of attributes, and wherein the attribute management system is further configured for:
detecting a duplicate attribute in the plurality of attributes based on analyzing the metadata of the plurality of attributes; and
causing the duplicate attribute to be removed from the plurality of attributes.

4. The system of claim 3, wherein detecting the duplicate attribute is performed based on one or more of source code of the attribute definitions, input data of the attribute definitions, results of computation of the plurality of attributes against a baseline input data set, or variables that the plurality of attributes depend on.

5. The system of claim 1, wherein the attribute development system is further configured for providing an annotation framework that contains fields for inputting annotations for the attribute definitions.

6. The system of claim 5, wherein the attribute management system is further configured for detecting metadata associated with the attribute definitions based on one or more of the annotations for the attribute definitions or source code of the attribute definitions.

7. The system of claim 6, wherein the attribute management system is further configured for comparing the plurality of attributes based on source code of the attribute definitions, the metadata associated with the attribute definitions, and outputs of the attribute definitions based on same input data.

8. A method that includes one or more processing devices performing operations comprising:
    accessing attribute templates and production data layouts, wherein the attribute templates are written in a production-ready programming language, and wherein the production data layouts specify layouts for data used in a production environment of a software program and the software program written in a programming language compatible with the production-ready programming language;
    determining a plurality of attributes based on analyzing input data using the attribute templates, the input data being organized according to the production data layouts;
    generating attribute definitions for the plurality of attributes using the attribute templates;
    deploying the attribute definitions for the plurality of attributes to the production environment of the software program;
    monitoring performance of the plurality of attributes in the production environment of the software program; and
    causing the attribute definitions of the plurality of attributes to be modified based on the monitoring.

9. The method of claim 8, wherein the attribute definitions are associated with metadata of the plurality of attributes, and wherein the method further comprises:
    analyzing the attribute definitions based on the metadata to generate an attribute dependency graph; and
    causing the attribute definitions to be modified based on the attribute dependency graph.

10. The method of claim 8, wherein the attribute definitions are associated with metadata of the plurality of attributes, and wherein the method further comprises:
    detecting a duplicate attribute in the plurality of attributes based on analyzing the metadata of the plurality of attributes; and
    causing the duplicate attribute to be removed from the plurality of attributes.

11. The method of claim 10, wherein detecting the duplicate attribute is performed based on one or more of source code of the attribute definitions, input data of the attribute definitions, results of computation of the plurality of attributes against a baseline input data set, or variables that the plurality of attributes depend on.

12. The method of claim 8, further comprising providing an annotation framework that contains fields for inputting annotations for the attribute definitions.

13. The method of claim 12, further comprising detecting metadata associated with the attribute definitions based on one or more of the annotations for the attribute definitions or source code of the attribute definitions.

14. The method of claim 13, further comprising comparing the plurality of attributes based on source code of the attribute definitions, the metadata associated with the attribute definitions, and outputs of the attribute definitions based on same input data.

15. A non-transitory computer-readable storage medium having program code that is executable by a processor device to cause a computing device to perform operations, the operations comprising:
    accessing attribute templates and production data layouts, wherein the attribute templates are written in a production-ready programming language, and wherein the production data layouts specify layouts for data used in a production environment of a software program and the software program written in a programming language compatible with the production-ready programming language;
    determining a plurality of attributes based on analyzing input data using the attribute templates, the input data being organized according to the production data layouts;
    generating attribute definitions for the plurality of attributes using the attribute templates;
    deploying the attribute definitions for the plurality of attributes to the production environment of the software program;
    monitoring performance of the plurality of attributes in the production environment of the software program; and
    causing the attribute definitions of the plurality of attributes to be modified based on the monitoring.

16. The non-transitory computer-readable storage medium of claim 15, wherein the attribute definitions are associated with metadata of the plurality of attributes, and wherein the operations further comprise:
    analyzing the attribute definitions based on the metadata to generate an attribute dependency graph; and
    causing the attribute definitions to be modified based on the attribute dependency graph.

17. The non-transitory computer-readable storage medium of claim 15, wherein the attribute definitions are associated with metadata of the plurality of attributes, and wherein the operations further comprise:
    detecting a duplicate attribute in the plurality of attributes based on analyzing the metadata of the plurality of attributes; and
    causing the duplicate attribute to be removed from the plurality of attributes.

18. The non-transitory computer-readable storage medium of claim 17, wherein detecting the duplicate attribute is performed based on one or more of source code of the attribute definitions, input data of the attribute definitions, results of computation of the plurality of attributes against a baseline input data set, or variables that the plurality of attributes depend on.

19. The non-transitory computer-readable storage medium of claim 15, wherein the operations further comprise providing an annotation framework that contains fields for inputting annotations for the attribute definitions.

20. The non-transitory computer-readable storage medium of claim 19, wherein the operations further comprise detecting metadata associated with the attribute definitions based on one or more of the annotations for the attribute definitions or source code of the attribute definitions.

* * * * *